United States Patent
Bartels et al.

(10) Patent No.: US 10,488,259 B2
(45) Date of Patent: Nov. 26, 2019

(54) APPARATUS AND METHOD FOR MEASUREMENT OF OPTICAL FREQUENCY SHIFTS

(71) Applicant: COLORADO STATE UNIVERSITY RESEARCH FOUNDATION, Fort Collins, CO (US)

(72) Inventors: Randy A. Bartels, Fort Collins, CO (US); David G. Winters, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 241 days.

(21) Appl. No.: 15/317,963

(22) PCT Filed: Jun. 10, 2015

(86) PCT No.: PCT/US2015/035072
§ 371 (c)(1),
(2) Date: Dec. 11, 2016

(87) PCT Pub. No.: WO2015/191690
PCT Pub. Date: Dec. 17, 2015

(65) Prior Publication Data
US 2018/0209851 A1    Jul. 26, 2018

Related U.S. Application Data

(60) Provisional application No. 62/011,126, filed on Jun. 12, 2014.

(51) Int. Cl.
*G01J 3/44* (2006.01)
*G01J 9/00* (2006.01)
(Continued)

(52) U.S. Cl.
CPC . *G01J 3/44* (2013.01); *G01J 3/10* (2013.01); *G01J 3/26* (2013.01); *G01J 3/433* (2013.01);
(Continued)

(58) Field of Classification Search
CPC ................ G01N 2021/653; G01J 2009/006
See application file for complete search history.

(56) References Cited

U.S. PATENT DOCUMENTS 4,972,331 A * 11/1990 Chance ............... A61B 5/1455
600/310
5,770,454 A     6/1998 Essenpreis et al.
(Continued)

FOREIGN PATENT DOCUMENTS

WO        2015191690        12/2015

OTHER PUBLICATIONS

PCT/US2015/035072 Search Report & Written Opinion, dated Oct. 8, 2015, 10 total pages.
(Continued)

*Primary Examiner* — Shawn Decenzo
(74) *Attorney, Agent, or Firm* — Maschoff Brennan; Paul G. Johnson (57) ABSTRACT

An apparatus and method for measuring small changes in the centroid of the spectrum of a light field by conversion of optical frequency centroid shifts into time delays are described. A time delay for a particular frequency of light is created by directing the light into an optically dispersive system that converts the change in center frequency to a change in transit time through the system as the dispersive element causes different colors to travel at different speeds. Examples of such dispersive elements include, but are not limited to, optical fibers, bulk materials, volumetric or fiber Bragg gratings, and grating or prism based pulse stretchers. This time delay can be measured, by detecting the change in
(Continued)

transit time (or time of flight through the dispersive element) by using a detector such as a photodiode, PMT, etc. that converts the incident optical pulse train into an electronic pulsed signal. The phase of the periodic electronic signal provides a measure of the timing delay of the pulse, and can be determined by adapting standard methods of electronic oscillator phase detection relative to a reference electronic oscillator clock.

25 Claims, 5 Drawing Sheets

(51) Int. Cl.
| | | |
|---|---|---|
| *G01J 3/10* | | (2006.01) |
| *G01J 3/26* | | (2006.01) |
| *G01J 3/433* | | (2006.01) |
| *G02B 26/00* | | (2006.01) |
| *G01N 21/65* | | (2006.01) |

(52) U.S. Cl.
CPC .............. *G01J 9/00* (2013.01); *G02B 26/001* (2013.01); *G01N 2021/653* (2013.01)

(56) References Cited

U.S. PATENT DOCUMENTS

| | | | |
|---|---|---|---|
| 6,813,948 B1 | 11/2004 | Rinn | |
| 2009/0073432 A1* | 3/2009 | Jalali | G01J 3/10 356/301 |
| 2010/0097613 A1 | 4/2010 | Saari | |
| 2015/0097118 A1* | 4/2015 | Zheng | G01J 3/42 250/339.07 |

OTHER PUBLICATIONS

E. N. Ivanov, S. A. Diddams, and L. Hollberg, "Analysis of Noise Mechanisms Limiting the Frequency Stability of Microwave Signals Generated With a Femtosecond Laser," IEEE J. Sel. Top. Quantum Electron., vol. 9, No. 4, pp. 1059-1065, 2003. 7 pgs.
F. Quinlan, T. M. Fortier, H. Jiang, A. Hati, C. Nelson, Y. Fu, J. C. Campbell, and S. A. Diddams, "Exploiting shot noise correlations in the photodetection of ultrashort optical pulse trains," Nat. Photonics, vol. 17, pp. 290-293, 2013 4 pgs.
J. Kim, F. X. Kartner, and M. H. Perrott, "Femtosecond synchronization of radio frequency signals with optical pulse trains.," Opt. Lett., vol. 29, No. 17, pp. 2076-2078, Sep. 2004 3 pgs.
W. Kim and A. Majumdar, "Phonon scattering cross section of polydispersed spherical nanoparticles," J. Appl. Phys., vol. 99, No. 8, p. 084306, 2006. 8 pgs.
K. Jung and J. Kim, "Subfemtosecond synchronization of microwave oscillators with mode-locked Er-fiber lasers.," Opt. Lett., vol. 37, No. 14, pp. 2958-2960, Jul. 2012. 4 pgs.
W. H. Steier, "A Push-Pull Optical Amplitude Modulator," IEEE J. Quantum Electron., vol. QE-3, No. 12, pp. 664-667, 1967. 4 pgs.
S. Dubovitsky, W. H. Steier, S. Yegnanarayanan, and B. Jalali, "Analysis and Improvement of Mach-Zehnder Modulator Linearity Performance for Chirped and Tunable Optical Carriers," J. Light. Technol., vol. 8724, No. May, pp. 886-891, 2002. 6 pgs.
T. M. Fortier, C. W. Nelson, a. Hati, F. Quinlan, J. Taylor, H. Jiang, C. W. Chou, T. Rosenband, N. Lemke, a. Ludlow, D. Howe, C. W. Oates, and S. a. Diddams, "Sub-femtosecond absolute timing jitter with a 10 GHz hybrid photonic-microwave oscillator," Appl. Phys. Lett., vol. 100, No. 23, p. 231111, 2012. 9 pgs.
J. Kim and F. X. Kartner, "Attosecond-precision ultrafast photonics," Laser Photon. Rev., vol. 4, No. 3, pp. 432-456, Apr. 2010. 25 pgs.
B. H. Kolner, "Generalization of the concepts of focal length and f-number to space and time," J. Opt. Soc. Am. A, vol. 11, No. 12, pp. 3229-3234, Dec. 1994. 6pgs.
C. V. Bennett, R. P. Scott, and B. H. Kolner, "Temporal magnification and reversal of 100 Gb/s optical data with an up-conversion time microscope," Applied Physics Letters, vol. 65, No. 20, pp. 2513-2515, Nov. 1994 3pgs.
B. H. Kolner, "Space-time duality and the theory of temporal imaging," IEEE J. Quant. Electron., vol. 30, No. 8, pp. 1951-1963, Aug. 1994. 13 pgs.
B. H. Kolner and M. Nazarathy, "Temporal imaging with a time lens," Optics Letters, vol. 14, pp. 630-632, 1989, and erratum vol. 15, p. 655, 1990. 4 pgs.
B. H. Kolner, "Active pulse compression using an integrated electro-optic phase modulator," Applied Physics Letters, vol. 52, No. 14, pp. 1122-1124, 1988 4pgs.
R. Salem et al., "Application of space-time duality to ultrahigh-speed optical signal processing" Adv. Opt. Photon. 5, 274-317 (2013) 45pgs.
S. A. Akhmanov et al., "Nonstationary phenomena and space-time analogy in nonlinear optics," Sov. Phys. JETP vol. 28, No. 4, 748-757 (Apr. 1969) 10pgs.
Agrawal, "Space-Time Duality in Optics", Institute of Optics, University of Rochester, 2015 36pgs.
D. H. Broaddus, M. A. Foster, O. Kuzucu, A. C. Turner-Foster, K. W. Koch, M. Lipson, and A. L. Gaeta, "Temporal-imaging system with simple external-clock triggering," Optics Express vol. 18, No. 13, 14262-14269 (Jun. 21, 2010) 8pgs.
Fridman, Moti, et al. "Demonstration of temporal cloaking." Nature, vol. 481, No. 7379, 2012, p. 62 7pgs.

* cited by examiner

APPARATUS AND METHOD FOR MEASUREMENT OF OPTICAL FREQUENCY SHIFTS

CROSS-REFERENCE TO RELATED APPLICATIONS

The present application claims the benefit of PCT Patent Application Number PCT/US2015/035072 for "Apparatus and Method for Measurement Of Optical Frequency Shifts" by Randy A. Bartels and David G. Winters, which was filed on Jun. 10, 2015, and of U.S. Provisional Patent Application No. 62/011,126 for "Method And Device For Measurement Of Optical Frequency Shifts" by Randy A. Bartels and David G. Winters, which was filed on Jun. 12, 2014, the contents of which applications are hereby specifically incorporated by reference herein for all that they disclose and teach.

FIELD

The present invention relates generally to measuring small changes in the power spectrum of a light field and, more particularly, to measuring small changes in the centroid of the power spectrum of a light field by converting optical frequency centroid shifts into time delays.

BACKGROUND

Detection of low concentrations of molecular or material impurities is needed for many scientific and industrial applications. Vibrational spectral techniques of Raman scattering and mid-infrared (MIR) absorption, as examples, are widely used for these purposes. Vibrational spectroscopy uniquely identifies molecules by recording intrinsic vibrational spectral features of the molecules. MIR imaging exhibits poor spatial resolution due to the long wavelengths, and presents challenges due to pervasive absorption and the poor quality of mid-infrared light sources and detectors. Although Raman microscopy uses visible or near infrared light, permitting high spatial resolution imaging, Raman interactions are weak, which limits Raman spectroscopic imaging to relatively high concentration levels. Doppler Raman spectroscopy is based on the measurement of small frequency shifts imparted to pulses in a short laser pulse train interacting with coherently excited Raman-active vibrational modes. That is, a short laser pump pulse is directed into a specimen containing molecules having Raman-active vibrational modes. This pulse is followed by a probe pulse that acquires a shift in the centroid of the pulse spectrum due to the coherently excited vibrations. Typical frequency shifts are tens of GHz; however detection of nanomole concentrations of molecules requires resolving shifts of about 500 Hz.

Other examples where measurement of small frequency shifts is required include, but are not limited to, other inelastic scattering processes, measurement of Doppler shifts, or spectrally-dependent absorption processes that reshape the electromagnetic pulse spectrum.

An electromagnetic pulse, such as an optical pulse, is composed of a broad set of frequencies, referred to as the optical spectrum. One characteristic of such a pulse spectrum is the center or centroid of the spectrum, which is generally the object of measurement. The most common method for measuring optical spectra is an optical spectrometer. The center wavelength (or frequency) can be determined by computing the centroid of the spectral distribution. Changes in the spectrum can be detected by re-measuring the spectrum and calculating the centroid of the modified spectrum.

The highest resolution spectrometers have a maximum resolution in the range of 1 GHz, which is orders of magnitude too coarse for the measurements we wish to make. As stated, many applications require detection of much smaller frequency shifts or changes in center wavelength. The target frequency shift might derive from a translation of the spectrum to higher or lower wavelengths, or could be due to a change in the centroid of the power spectrum through some other mechanism that reshapes the spectrum of the light used to probe a physical behavior or interaction.

SUMMARY

Embodiments of the present invention overcome the disadvantages and limitations of prior art by providing an apparatus and method for measuring small changes in the centroid of the power spectrum of a light field.

Additional objects, advantages and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the method for measuring the shift in the center optical frequency of light from a light source, from that of a known center optical frequency, hereof, includes: directing the light from the light source into an optically dispersive system, whereby the center frequency experiences a first transit time through the dispersive system; measuring the first transit time; directing the known center optical frequency into the optically dispersive system, whereby the frequency of the known center frequency experiences a second transit time through the dispersive system; measuring the second transit time; and generating a time delay from the difference of the first transit time and the second transit time; from which the shift in the center optical frequency is determined.

In another aspect of the present invention, and in accordance with its objects and purposes, the apparatus for measuring the shift in the center optical frequency of light from a light source, from that of a known center optical frequency, hereof, includes: an optically dispersive system for receiving light from said light source, whereby the center optical frequency travels through the dispersive system in a first time period, different from the time of travel of the known center optical frequency through the dispersive system; and means for measuring the first time period; whereby the difference in the first time period from that of the known center optical frequency is determined.

In yet another aspect of the present invention, and in accordance with its objects and purposes, the method for measuring the shift in the center optical frequency of light from a light source, from that of a known center optical frequency, hereof, includes: directing the light from the light source into an optically dispersive system, whereby the center frequency experiences a first transit time through the dispersive system; and measuring the first transit time.

Benefits and advantages of the present invention include, but are not limited to, an apparatus and method for measuring small changes in the centroid of the power spectrum of a light field by conversion of optical frequency centroid shifts into a time delays, which permits significantly higher sensitivity than the most sensitive Raman sensing techniques.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 10a is a graph of the Raman signal measured as a function of pump-probe delay using the Optical PLL (solid curve), the temporal data being processed using the Linear Prediction Singular Value Decomposition, LPSVD, algorithm, which determines the phases, amplitudes, and damping coefficients of a data set containing a linear combination of exponentially decaying sinusoids, and the predicted trace plotted (dotted), while

DETAILED DESCRIPTION OF THE INVENTION

Embodiments of the present invention include an apparatus and method for measuring small changes in the centroid of the spectrum of a light field by conversion of optical frequency centroid shifts into a time delay. This time delay is created by sending the light into an optically dispersive system that then converts the change in center frequency to a change in transit time through the system as the dispersive element causes different colors (i.e., wavelengths, or frequencies) to travel at different speeds. Examples of such dispersive elements include, but are not limited to, optical fibers, bulk materials, volumetric or fiber Bragg gratings, and grating or prism based pulse stretchers. This time delay can then be measured, by adapting techniques used for directly determining the timing jitter of optical pulses, examples of which include Optical PLL and intensity (balanced or not balanced) cross (or auto) correlation. Another approach for detecting the change in transit time (or time of flight through the dispersive element) is to use a detector such as a photodiode, PMT, etc. that converts the incident optical pulse train into an electronic pulsed signal (current or voltage). The phase of the periodic electronic signal provides a measure of the timing delay of the pulse. This electronic phase can be determined by adapting standard methods of electronic oscillator phase detection, that is, one can detect the phase of the electronic signal out of the detector relative to a reference electronic oscillator clock. These systems are similar to those used for the measurement of timing jitter of mode locked laser oscillators.

Thus, changes in the centroid of the optical spectrum lead to changes in the transit time through the dispersive delay system. To enhance sensitivity in the detection of these transit delays, from which center frequency changes are inferred, the process that causes the change in the center wavelength of the optical pulse train center frequency is modulated, and the modulated change in the pulse transit time (and the RF phase) is detected using a lock-in amplifier. To demonstrate embodiments of the present invention, frequency shifts imparted to optical pulses in a pulse train due to coherent Raman scattering, are measured in time as a phase shift in the electronic impulse train generated by a photodetector by an incident optical pulse train. It should be noted that an "electronic impulse train" results for incident pulses that are shorter than the impulse response of the photodetector, but these pulses do not need to be shorter than the impulse response of the photodetector.

Coherent Raman scattering will be used as an example of the principles of this invention. Pulses from a mode locked laser oscillator were split into a pump pulse and a probe pulse. The pump pulse was sent through a modulator that imparted a time-dependent intensity modulation on the pump pulse train. The pump and probe pulses are focused into a sample having Raman-active vibrational modes. The probe pulse is time-delayed from the pump pulse. The pump pulse excites coherent vibrations in the molecule through impulsive stimulated Raman scattering (ISRS), which produces a time-varying index of refraction in the specimen. The probe pulse spectrum is modified during propagation through the coherently excited vibrations, spectrum modulation occurring with a temporal signature determined by the intensity modulation pattern applied to the pump pulse train. The time-dependent spectral changes produce a time-varying modification of the centroid of the probe pulse spectrum, which change in centroid is detected in accordance with the teachings of embodiments of the present invention.

Of note is that instead of using an intensity modulated pump pulse, the probe pulse could operate at a higher repetition rate than the pump pulse train, wherein the difference in repetition rates produces a modulation rate of the coherent Raman scattering induced frequency shift, which is then measured in time as a phase shift in the electronic impulse train.

As stated above, coherent Raman scattering is one example of the application of embodiments of the invention, but many other measurements will benefit from this technology. For example, optical interactions that change the power spectrum that is to be measured, for example, spectral shape changes from transient absorption can benefit from the present apparatus and method.

In what follows, measurement of small shifts in the centroid of optical spectra, including those cases in which the center frequency modulation applied to each pulse is the same, will be described. As stated above, measurement of a frequency shift generated by the transient index of refraction in a Raman active material produced by impulsive nonlinear excitation is exemplified, but the system may be applied to any experiment in which changes in the center frequency of a spectrum arise, like cross-phase modulation or transient absorption. While such spectral changes are common in the case of short pulse laser systems, the measurement could also be applied to broadband incoherent pulsed illumination sources that undergo a change in the centroid of the electromagnetic spectrum.

A double balanced mixer using a reference oscillator was employed as a phase detector in the demonstration of embodiments of the present method, but any phase measurement system may be implemented, including direct pulse train measurement, a single-source measurement using a frequency discriminator, or a lock-in amplifier. A direct time measurement system including, for example, one that functions by direct sampling or edge counting, may also be employed. Several methods for the measurement of delay are described, but these methods are not exhaustive. Any device that measures the delay of the pulse train (or, equivalently, the RF phase change of an electronic signal generated by the pulse train detected by the photodetector) can be implemented to perform the measurement. The methods detailed herein may be modified from what is described with similar results.

I. Frequency Shift to Time Delay Conversion:

The method for measurement of the Raman-induced frequency shift is based on measurement of time delay. As direct measurement with a grating spectrometer is limited by spectrometer resolution to about a gigahertz.

Reference will now be made in detail to the present embodiments of the invention, examples of which are illustrated in the accompanying drawings. In the FIGURES, similar structure will be identified using identical reference characters. It will be understood that the FIGURES are for the purpose of describing particular embodiments of the invention and are not intended to limit the invention thereto. Turning now to FIGS. 1a-1f, a schematic representation of frequency shift to time delay conversion is shown. Optical pulse train, 12, illustrated in FIG. 1a acquires a shift in center frequency, shown for 2 different shifts in FIG. 1b, after propagation through optical fiber dispersive element, 14, shown in FIG. 1c, which introduces a time delay on the pulse train when it is collected on a photodiode (PD), 16, illustrated in FIG. 1e. The electronic pulse train spectrum shown in FIG. 1d, comprises a series of harmonics of the repetition rate, which can be separated through electronic filtering, as in the first and third harmonics shown in FIG. 1f.

Figure 1:
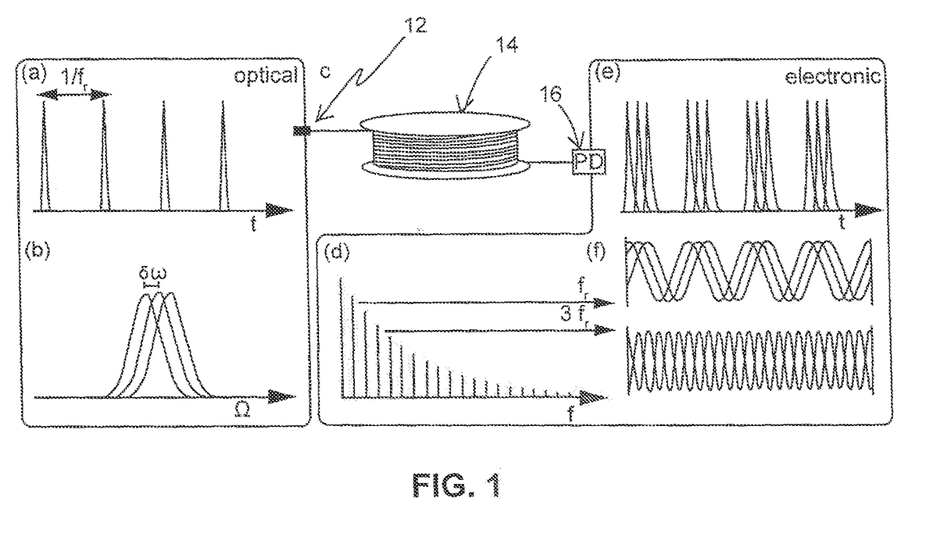
FIGS. 1a-1f are schematic representations of an embodiment of the frequency shift to time delay conversion of the present invention, wherein optical pulse train in FIG. 1a acquires a shift in center frequency, shown for 2 different shifts in FIG. 1b, and propagation through a dispersive element, such as an optical fiber FIG. 1c, introduces a time delay on the pulse train when it is collected on a photodiode, PD shown in FIG. 1e, FIG. 1d showing the electronic pulse train spectrum comprising a series of harmonics of the repetition rate, which can be separated through electronic filtering, as in the first and third harmonics shown in FIG. 1f.
Figure 2:
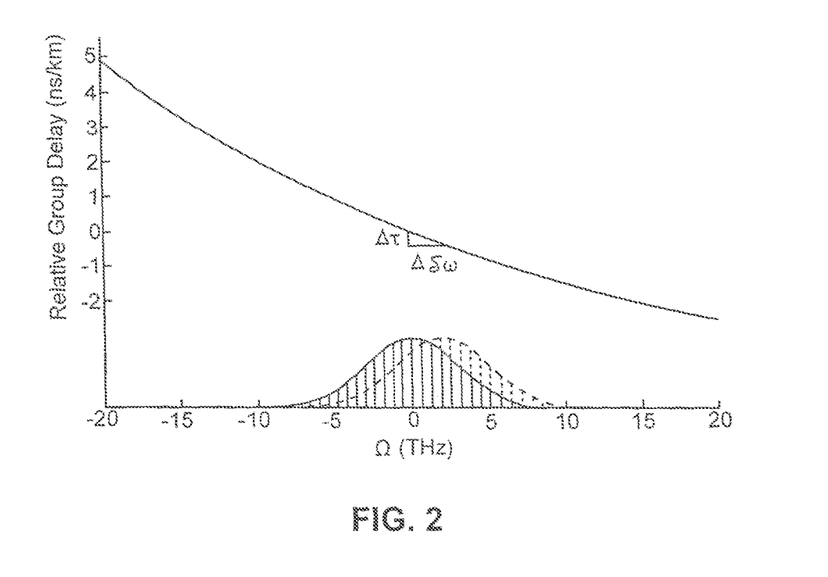
FIG. 2 is a graph of the time delay, $\Delta\tau$, induced by a shift in center frequency, $\Delta\omega$, of a pulse in a fused silica glass dispersive material centered at 1550 nm.

Thus, the shift in optical frequency of an ultrafast pulse is converted into a time delay through the application of dispersion. Since ultrafast pulses include many colors of light, when the pulses travel in a dispersive material or system, these different colors travel at different speeds. When the pulse exits the material, it will have experienced a time delay proportional to the center frequency, as shown in FIG. 2, which is a graph of the time delay, $\Delta\tau$, induced by a shift in center frequency, $\Delta\omega$, for a pulse in a fused silica glass dispersive material centered at 1550 nm. It should be mentioned that any pulse center wavelength (or frequency) could be used. Moreover, a pulse train of THz, mm wave, or microwave pulses can also be used.

Mathematically, the pulse propagation through a material can be expressed in terms of acquisition of a spectral phase, which we can write as a Taylor expansion $\phi(\Omega)=\phi_0+\phi_1\Omega+\frac{1}{2}\phi_2\Omega^2+\ldots$ higher-order terms. The transit time of a pulse through the system is given by the group delay, $\tau_g=\partial\Phi(\Omega)/\partial\omega$. The group delay can then be written in terms of the dispersion as $\tau_g=\phi_1+\phi_2\Omega$, where terms beyond second order have been truncated, as it is expected that $\phi_2$ will dominate the change in group delay. Thus, the transit time will change with a change in center frequency as $\Delta\tau_g=\phi_2\delta\omega$. More generally, $\Delta\tau_g=(\partial\Phi(\Omega)/\partial\omega)\delta\omega$.

Thus, a time delay (or transit time through the dispersive system) proportional to the frequency shift, which is in turn proportional to the Raman response, remains, and the measurement of the optical frequency shift has been transformed to the measurement of small time delays in accordance with the teachings of embodiments of the present invention. To measure the shift in the centroid of the spectrum, procedures for measuring pulse train delay. Examples, which will be described in detail below, include:

(a) Direct Pulse Train Measurement:

Phase detection of harmonics of the oscillator pulse train is employed, where a portion of the power of the probe pulse train is directed onto a photodetector, and the probe pulse once it has been frequency shifted is directed onto a separate photodetector. The phase of the electronic signal generated by the photodetector with the unperturbed probe pulse train incident is then compared to the electronic signal generated by the perturbed probe pulse train. The difference in the electronic phase of the probe pulse train repetition rate (or a harmonic of the repetition rate) is used to determine the transit time delay through the dispersive system, which is used to determine the change in the pulse center frequency.

(b) Nonlinear Optical Cross Correlation:

This procedure will turn a small timing change into an amplitude change of the autocorrelation signal, but has been found to have poor sensitivity to frequency shifts.

(c) Optical PLL (Optical Phase-Lock Loop):

This well-known procedure also turns the time delay signal into a power signal, but by utilizing an electro-optic intensity (or phase) modulator, which will enable an RF oscillator to be phase locked to the pulse train. The measurement of this timing change is then made as an RF phase measurement, wherein the task of measuring $\delta\omega$ is translated into the measurement of $\delta\phi_{RF}$. Such phase measurements can be made very accurately, whereby this technique has a detection limit much lower than systems which measure power directly. Use is made of one or two optical modulators (Reference [9]) to generate a change in optical transmission through a system while providing a measure of the pulse train timing jitter. Adaptation has been made of one of these modulators to measure changes in transit time, rather than timing jitter.

Figure 3:
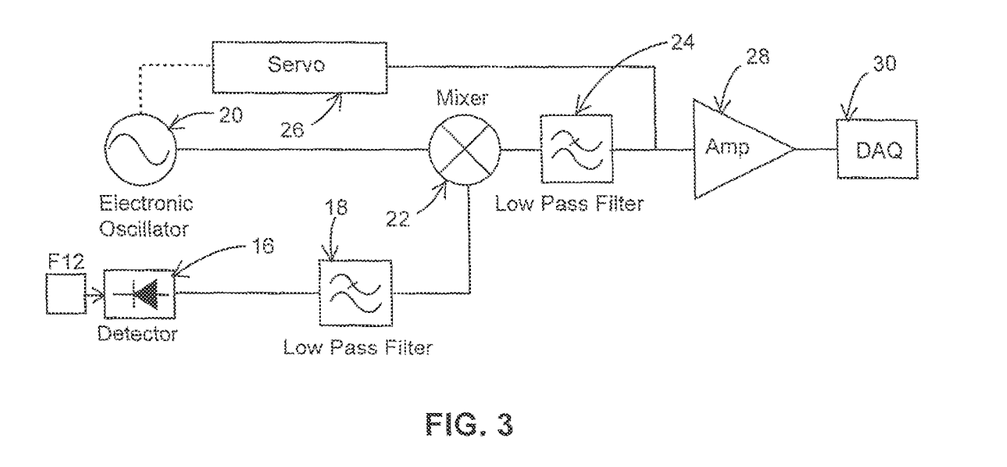
FIG. 3 is a schematic representation of an embodiment of an apparatus for measuring phase.

II. Direct Pulse Train Measurement:

As stated, in the simplest apparatus for detecting the transit time changes to determine center spectrum changes, the optical pulse train is converted to an electronic pulse train using a photodetector. An apparatus for phase measurement is illustrated in FIG. 3. It should be mentioned that phase detection is well known, and that there are commercial systems available including those packaged in integrated circuits. The noise floor of the present measurement will be dictated by the noise floor of the phase detection method employed. Detector 16, which may be a photodiode a photomultiplier tube, as examples, converts optical pulses 12 to electronic pulses. Filter, 18, converts the electronic pulse train into a sinusoid, the arrival time of the pulses now being the phase of the electronic sine wave. Output from voltage controlled oscillator, 20, having the same frequency as the optical pulse repetition rate is then mixed with the sinusoid in mixer, 22, which multiplies the two signals. Low-pass filter, 24, removes the sum frequency, leaving a voltage signal proportional to the phase difference between the signal from oscillator 20 and the signal from detector 16. Since reference oscillator 20 operates at exactly the same frequency as the laser repetition rate, a feedback loop using Servo, 26, controls electronic oscillator 20 to ensure that it operates at the correct frequency. The difference frequency output from filter 24 may be amplified using amplifier, 28, and digitized or otherwise processed in data acquisition system, 30.

The electronic pulses in the electronic signal have a shape given by the convolution in time of the impulse response of the photodetector and the shape of the pulse intensity in time (for optical pulses). This periodic electronic signal has a fundamental periodicity that is the same as the incident probe pulse train repetition frequency. The electronic signal can be filtered to extract a signal component centered at the repetition rate or a harmonic of the repetition rate (with the number of harmonics present limited by the bandwidth of the photodetector). The timing change in the pulse train maps to a phase shift in this sinusoidal signal, which is measured using an electronic phase detector. This phase change is the signal of interest, as it gives a measurement of the frequency shift as $$\Delta\phi_{RF}=2\pi m\, f_r \Delta\tau = 2\pi m\, f_r \phi_2 \delta\omega$$

where m is the chosen harmonic of the repetition rate frequency, $f_r$. The performance of this measurement system is degraded by noise introduced by the photodetector, as well as noise present in the phase locking setup. Amplitude noise measured on the photodiode will manifest as white phase noise, or other noise, written onto the locked oscillator [1]. The shot noise limited phase noise, converted from [1] is $$S_\phi(f) = \frac{P_{shot}}{P_{signal} f_B},$$

which can be expressed in dBr/Hz. In this equation, $P_{signal}$ is the power of the microwave signal from the photodiode at the desired harmonic m of the repetition rate frequency $m\, f_r$, and $P_{shot}=2\, q\, f_B R_p P_d\, R$ is the shot-noise power of the light incident on the photodiode, where q is the electron charge, $f_B$ is the measurement bandwidth, $R_p$ is the photodiode responsivity, $P_d$ is the average power incident on the photodiode, and R is the load impedance.

This expression is based on the shot noise as a result of average power incident on the photodiode. In more recent work [2], correlations in the measured shot noise of short pulse trains were used to operate at shot-noise limited levels several orders of magnitude below that predicted using the average power. These experiments made use of a new class of fast photodiodes with high power handling, and distinct from those used in the present patent application, and could be used to further boost the sensitivity of frequency shift detection using the teachings of embodiments of the present invention.

Figure 4:
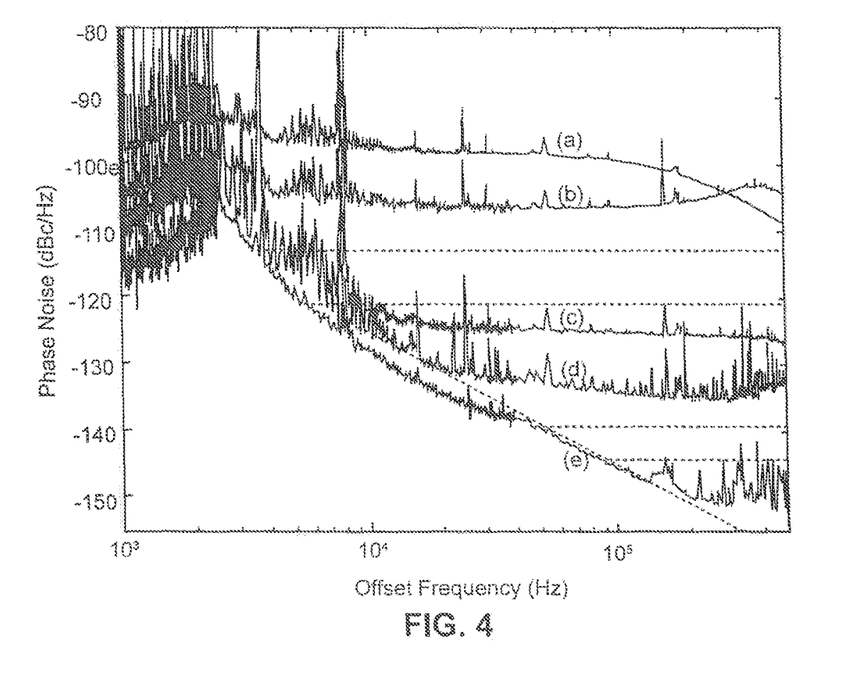
FIG. 4 is a graph of the measured phase noise floor of the pulse train incident on a single diode for different power levels generated by the apparatus of FIG. 3, hereof, wherein curve (e) shows the measured phase noise floor of the reference oscillator, with the sloped dashed line giving the expected noise floor.

To quantify the noise floor in the single-detector measurement using the apparatus of FIG. 3, the frequency shifted pulses are coupled into a ~20 km length of optical fiber and the pulse train is detected using a photodiode (Thorlabs DET10C). FIG. 4 is a graph of the single-sideband phase noise of the repetition rate measured using a phase detector. This measurement is made for several power levels ((a) 26 µW; (b) 97 µW; (c) 305 µW; and (d) 1.04 mW), and plotted alongside the shot-noise limited noise floor calculated for each power level (dashed curves).

As the photodiode signal was not sufficient to drive the mixer in the phase measurement setup, RF amplifier (Mini-circuits ZHL-3010) 28 in FIG. 3 was used which provided 30 dB gain with a 6 dB noise figure. This accounts for some of the degradation of the expected performance (as the plotted theoretical floor does not account for the noise figure of this amplifier), though the difference between the measurement and the expected value is close to 14 dB. The additional 8 dB is likely due to excess noise coming from amplitude to phase noise conversion in the photodiode and in the mixer, as well as noise generated by propagation through the apparatus and through the long fiber.

III. Optical Phase-Locked Loop:

The Direct Pulse Train Measurement method directly converts the optical probe pulse train into an electronic signal pulse train. One limitation for the sensitivity of this approach is that optical detectors introduce excess phase noise into the electronic signal (called amplitude-to-phase noise conversion). In order to reduce the impact of this amplitude-to-phase noise, and lower the noise floor of the measurement, a system which is less dependent on the impact of the photodetector [3] was tested. Two opposing signals are balanced to cancel out common amplitude noise. The cancelation does not require a nonlinear process, and thus, the chirped pulses will have less of an impact on the overall stability of the measurement. A similar technique that uses a single optical phase modulator that could also be used (See, e.g., Reference [9]).

Figure 5:
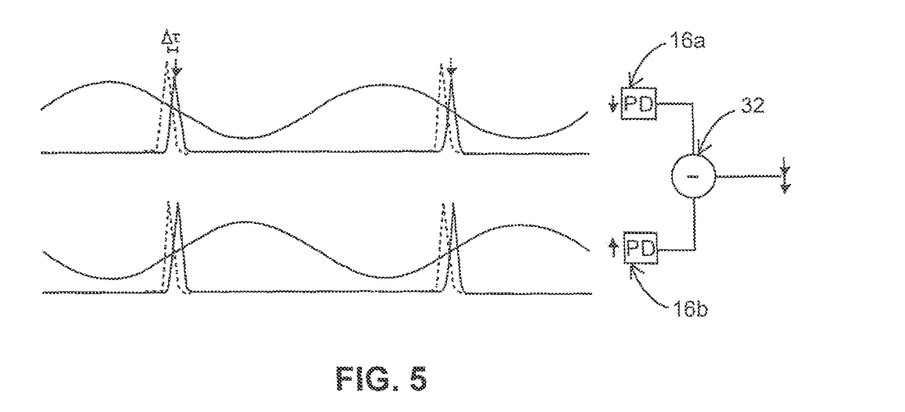
FIG. 5 is a schematic representation of the drive signals in the Optical PLL, where amplitude modulation is applied to two copies of the pulse train, $\pi$ out of phase, thereby generating an error signal that doubles the dependence on $\Delta\tau$ while cancelling any common mode noise on the pulse train.

An improvement in the noise was obtained using the so-called Optical PLL, which employs optical intensity modulators driven by an electronic reference oscillator to generate an error signal by attenuating the pulse train at the repetition rate. As will be described in more detail below, the input optical pulse train is divided in half, and each half is amplitude modulated using sinusoidal modulations out of phase with each other by π, as shown in FIG. 5. The modulated pulse trains are then measured on photodetectors 16a and 16b, and the difference signal is generated by summing amplifier, 32. In this way, small changes in the arrival time of the pulses will result in a small decrease in one signal and a small increase in the other, and the difference signal will then show a change proportional to twice the time change, while any amplitude noise common to both channels will be removed. The difference signal serves as an error signal which is fed back to a servo controlling the frequency of the microwave oscillators.

The Optical PLL apparatus is a variation of the apparatus illustrated in FIG. 3. The electronic components and additional optical components used for the Optical PLL are shown in the block diagram in FIG. 6. Raman-shifted probe pulses 12 are coupled into the optical fiber 14 (Corning SMF-28e). The light is then divided into the two channels using −3 dB fiber splitter, 34, each output channel of the fiber splitter, 36a, and, 36b, being spliced to the input of a lithium-niobate amplitude modulators (JDSU), 38a, and, 38b, respectively. The amplitude modulators only operate on one polarization, so the input fiber is laid in a polarization controller (General Photonics), which is used to project as much light as possible on the active polarization axis of the modulator. The light is collected with a pair of InGaAs photodiodes (Thorlabs DET10C), 16a and 16b, respectively, and the difference signal generated with summing amplifier (SRS SIM980), 32. This difference signal is the error signal, which is coupled into the input of the Servo (Vescent Photonics), 40. The output of servo 40 is the reference voltage for a VCO (Minicircuits ZX95-890C), 42, that drives amplitude modulators, 38a and 38b.

Figure 6:
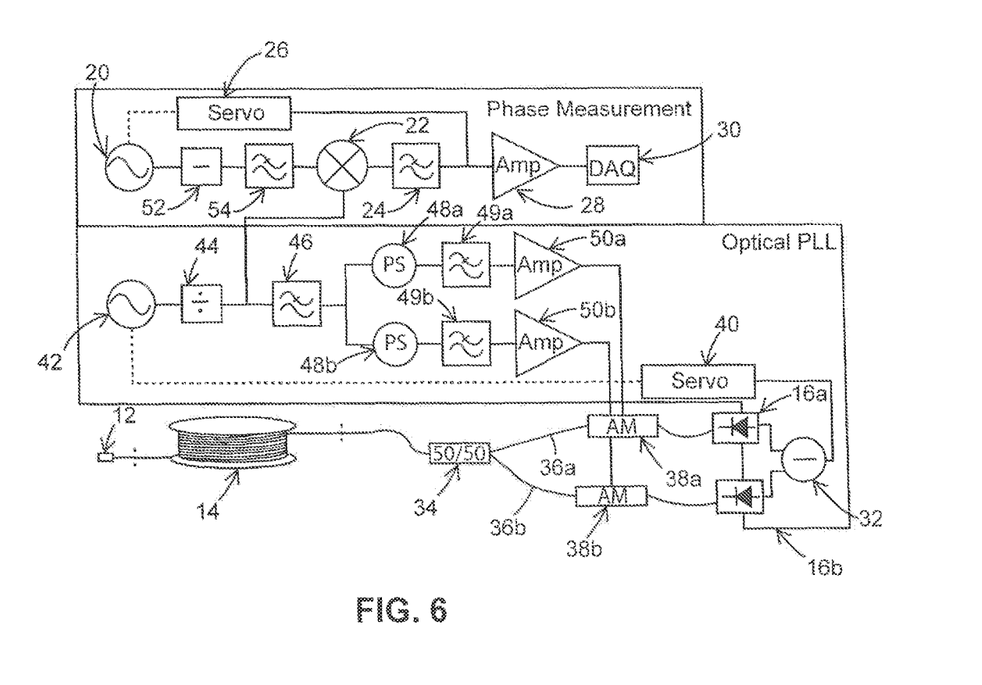
FIG. 6 is a schematic representation of another embodiment of the present apparatus for measuring phase, where the pulse to be measured enters the fiber dispersive element, propagates through the fiber, is divided 50/50 and modulated before being detected on matched photodetectors.

Modulators 38a and 38b are driven with a sine wave at the repetition rate, with the phase of the electronic signals being adjusted such that the pulses are sampling the peak slope of the attenuation of the modulators on both the rising and falling signals. This signal is generated from VCO 42 that is divided using divider, 44 (Valon 3008), before being separated into two channels by divider, 46 (Minicircuits ZFRSC-42), each of which goes into a voltage variable phase delay, 48a, and, 48b, (Minicircuits JSPHS-51) before being filtered, 49a, and, 49b, to remove any distortion caused by the phase shifters, and amplified with a low-noise power amplifiers, 50a, and, 50b (Minicircuits ZX60-100VH+), respectively. The amplified VCO signals are then connected to the RF input of amplitude modulators 38a and 38b, respectively. To initiate the locking, the VCO 42 is first locked to the pulse train using a photodiode collecting the residual pump light. This puts VCO 42 at the nominal repetition rate, allowing adjustment of the variable phase delays. The delays are used to ensure that the drive signals relative to the optical pulse train maintain a 180° offset. Once the proper phase delays are achieved, the error signal from the Optical PLL is restored, and the frequency lock is initiated. The divided output from VCO 42 is than mixed with the divided, 52, and filtered, 54, signal from VCO 20, and the phase is measured.

The phase noise of VCO 42 may be measured by mixing with a tracking oscillator using the "Phase measurement" block in FIG. 6, where VCO 20 tracks VCO 42 using Servo 26. Divider 52 is employed since, as the VCO 20 may be operating at a harmonic of the repetition rate (for phase noise reasons), in addition to low-pass filter 54 following divider 52 since the divider outputs square waves, and a sine wave is beneficial, although not necessary.

Figure 7:
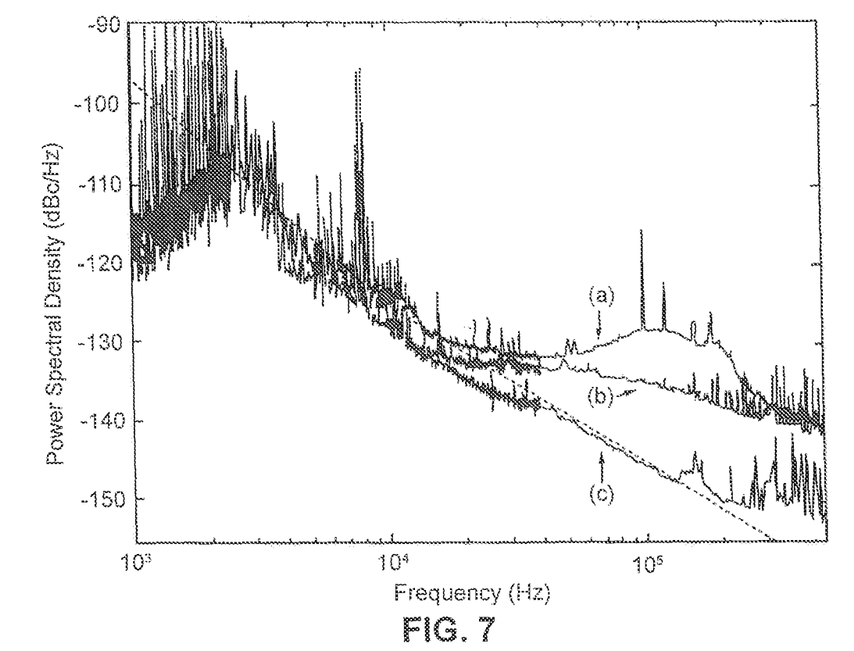
FIG. 7a is a graph of the laser noise measured using Optical PLL with the dispersive delay line.
FIG. 7b shows the noise without the dispersive delay line.
FIG. 7c illustrates the measured VCO phase noise floor, which is in good agreement with the expected value, shown as a dashed line.

To test the performance of the Optical PLL system, the pulse train is coupled into a short length of fiber, bypassing the dispersive delay line. This permits the performance of the measurement system to be characterized by observing the timing jitter of the laser oscillator alone, which will provide a limit on the performance of the system. The other limit will be imposed by the electronics used in the measurement system. The phase noise PSD is shown in FIG. 7 with and without the dispersive delay line. The phase noise floor reached about −130 dBc/Hz, limited in this case by optical power incident on the detector. The influence of the dispersive delay line can be seen in the difference between the two noise floors, as there is a slight decrease in noise when the long fiber is removed, likely due to the increase in optical power (as the loss in the fiber is ~0.2 dB/km). The other difference of note is the prominent gain peak that can be seen at about 100 kHz, due to the increased gain necessary to compensate for the fiber loss. The noise floor could be reduced by increasing the power at the detector, which could be accomplished at several points in the experiment. The amplitude modulators themselves introduce about 5 dB of loss, though modulators with only 3 dB of loss are commercially available. The transmission of the objectives used to focus onto the sample is quite low at our wavelength, as they objectives were designed for visible light, so the focusing and collection efficiency could be vastly improved by better matching the optics to the laser.

Figure 8:
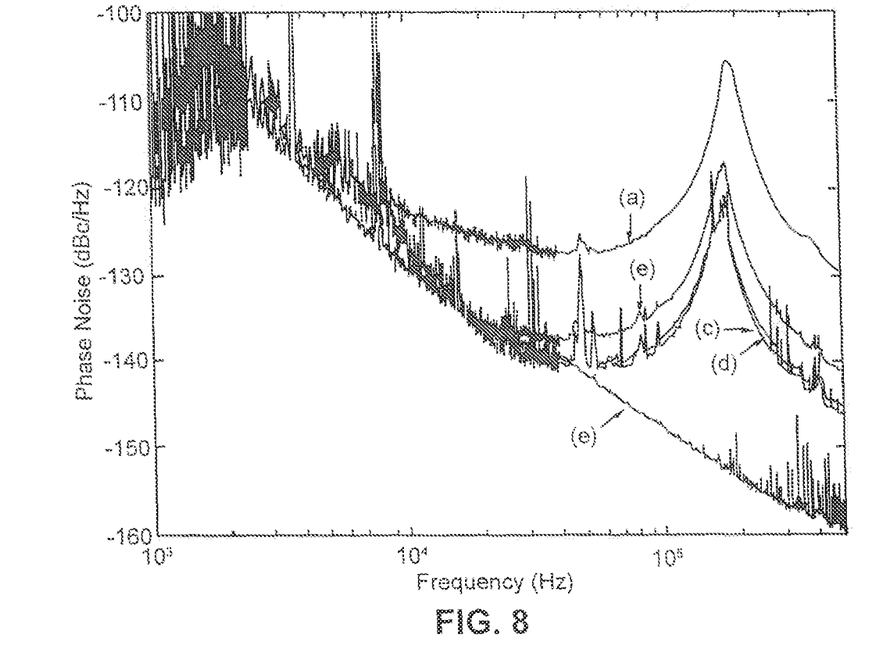
FIG. 8 is a graph of the phase noise floor for the Optical PLL system, showing a decrease in noise as power increases for the first few power levels, after which the noise floor does not fall off with power, but rather is limited by excess noise introduced by the detection process.

To examine further the impact of power on the Optical PLL, the laser beam is coupled directly into the long optical fiber. The power into the fiber is varied using a variable attenuator and measure the phase noise floor. The experimental setup and powers used in this data set are the same as those used in the single diode case, shown in FIG. 3. The power will be shown to impact the noise floor, and as power is shifted continuously from the pump to the probe arm to investigate the effect of lower pump powers, the predicted shot-noise limited phase noise will be shown to be a function of pump (probe) power. The results are shown in FIG. 8, and for the first two measurements show a decrease in noise floor with increasing power, as expected. However, further increases in power do not result in changes to the noise floor, as the noise floor is now being limited by some other component that has dominated the shot noise contribution, likely excess noise from the servo controller's output stage, as voltage noise on the output stage will manifest as phase noise on the VCO signal. The power levels used are the same as used in FIG. 4 to allow direct comparison. The distinct peak at high offset frequency is due to the limited bandwidth of the Servo at this high gain level.

While the performance of the Optical PLL has not reached the theoretical shot-noise limited levels, the technique could still be quite sensitivity in spite of the higher noise floor shown in FIG. 8. As can be seen, there is a prominent gain peak shown near the high frequency edge of the measured data. With higher optical powers, and thus higher RF powers, lower gain levels may be used in the feedback loop, providing for a larger, flatter gain spectrum lessening the gain peak in the measured phase noise. The phase noise may also be reduced by replacing the optical detectors with those able to operate at higher power, as in Reference [2], or by varying the optical power and measuring the amplitude to phase noise conversion to ensure it is minimized, as in Reference [8]. Both of these procedures reduce the noise to be canceled by the Optical PLL.

Reference [9], which describes a single modulator, might be useful for improving noise, since the optical properties of the two modulation paths would be identical, which assists in noise cancellation.

In the Optical Phase-Locked Loop phase measurements, amplitude noise being written to the error signal is avoided, as the two error signals vary with opposite signs with respect to timing jitter, but will react in the same way to amplitude noise. Taking the difference between these signals as the error signal gives rejection of common amplitude noise while doubling the dependence on timing jitter. Using this method, Kim et al. measured an RMS timing jitter of 2.4 fs (integrated from 1 mHz to 1 MHz [4]. More recently, Jung and Kim measured an RMS timing jitter of 0.847 fs (integrated from 1 Hz to 1 MHz) [5].

The sensitivity of the Optical PLL method is determined by considering the difference signal taken between two photodiodes, measuring pulse trains with intensity modulation driven by sine waves at the repetition rate, but 180° out of phase with one another. Following the similar derivation in Reference [4], the unmodulated pulse train has the form $$P_{in}(t) = \frac{P_{avg}}{f_r} \sum_{-\infty}^{\infty} \delta\left(t - \frac{n}{f_r}\right),$$

where $P_{avg}$ is the average power. The fiber amplitude modulator considered here is a Mach-Zehnder set up in a push-pull configuration[6]. The applied voltage to the modulator changes the phase relationship between the light in the two arms of the internal interferometer, leading to a transmission given by $$T_M = \frac{1}{2}\left[1 + \cos\left(\frac{\pi V}{V_\pi} - \phi_b\right)\right],$$

where $V_\pi$ is the voltage required to shift the modulator phase by $\pi$, e.g., the voltage difference between minimum and maximum attenuation, and is determined by the design of the modulator [7]. The bias phase $\phi_b$, is typically set to $\pi/2$ so that the modulator operates in a quasi-linear regime. Driving the modulator with a sinusoidal voltage, V at the chosen harmonic of the repetition rate, m $f_r$, leads to a power transmission that can be written $$P_{out}(t) = P_{in}(1 - \alpha_M)\left\{\frac{1}{2} + \frac{1}{2}\sin\left[\pi \frac{V_0}{V_\pi}\sin(2\pi m f_r t + \Delta\phi + \phi_e)\right]\right\},$$

where $P_{in}$ is the input power, $\alpha_M$ is the insertion loss of the modulator, $\phi_e$ is the phase change to be measured, and $\Delta\phi$ is the phase difference between the modulation signals. We'll define the phase depth as a function of the sine wave voltage amplitude $V_0$ and $V_\pi$ as $\Phi_0 = \pi V_0/V_\pi$. We can then write the power in each channel, where we have set $\Delta\phi = \pi$ such that the pulse train is sampling the positive and negative slopes of the driving sine wave. The power in each channel can be written $$P_{\pm}(t) = P'_{avg}/f_r \sum_{-\infty}^{\infty} \alpha_M \left\{\frac{1}{2} \pm \frac{1}{2}\sin[\Phi_0 \sin(2\pi m f_r t + \phi_e)]\right\} \delta\left(t - \frac{n}{f_r}\right),$$

where $P'_{avg} = (1-\alpha_M)P_{avg}$ is the power coupled into the modulator. We'll sample this modulation at the zero crossing, so we can substitute $$t = \frac{n}{f_r}$$

and write the average current from the photodiode for each channel is then given in terms of the photodiode responsivity, $R_p$, as $$\langle I_+ \rangle = R_p P'_{avg}\left\{\frac{1}{2} + \frac{1}{2}\sin[\Phi_0 \sin(\phi_e)]\right\}$$

$$\langle I_- \rangle = R_p P'_{avg}\left\{\frac{1}{2} - \frac{1}{2}\sin[\Phi_0 \sin(\phi_e)]\right\}$$

The difference signal is then Equation 1
$$\langle I_d \rangle = \langle I_+ \rangle - \langle I_- \rangle = R_p P'_{avg} \sin[\Phi_0 \sin(\phi_e)]$$

As the phase error $\phi_e$ is assumed to be small, we can presume that we are operating in the small-angle limit, and thus approximate $\langle I_d \rangle = R_p P'_{avg} \Phi_0 \phi_e$.

The phase detection sensitivity, $K_d$, can be written from Equation 1 as, $K_d = \langle I_d \rangle / \phi_e = R_p P'_{avg} \Phi_0$. This method will again be fundamentally limited by shot noise, now shot noise of the detected sinusoidally modulated power. The shot noise current density, in A²/Hz, is given by $S = 2qI = q R_p P'_{avg}$. This current density can be converted to a phase noise spectral density, rad.²/Hz, by dividing by the square of the phase detection sensitivity, $K_d$, giving $$S_{\varphi, I_{shot}} = \frac{S}{K_d^2} = \frac{q}{R_p P'_{avg}} \Phi_0^2,$$

where q is the charge of an electron. This power spectrum is a white noise process limited by the photocurrent, but with the added dependence on $\Phi_0^2$. Like the single diode case, this noise floor can be reduced by increasing the average power or the photodiode responsivity. Where this is advantageous over the single diode case is the dependence on $\Phi_0$. We can increase $\Phi_0$ to decrease the shot-noise limited floor below the single-diode case by increasing the RF power. This method is also not as influenced by amplitude to phase noise conversion, as common amplitude noise is canceled by the differential detection.

This analysis has presumed that the noise is dominated by the shot noise on the error signal. While this is the fundamental limit, the measured noise floor will always be the sum of all relevant noise sources. If the noise of some component exceed the shot-noise, for example from one of the oscillators, then the noise of that oscillator will dominate and appear as the noise floor. We will now estimate the magnitude of the shift that will be visible for some given noise floor, be it limited by oscillator phase noise, noise introduced by the error signal, or by timing jitter from the laser itself.

Figure 9:
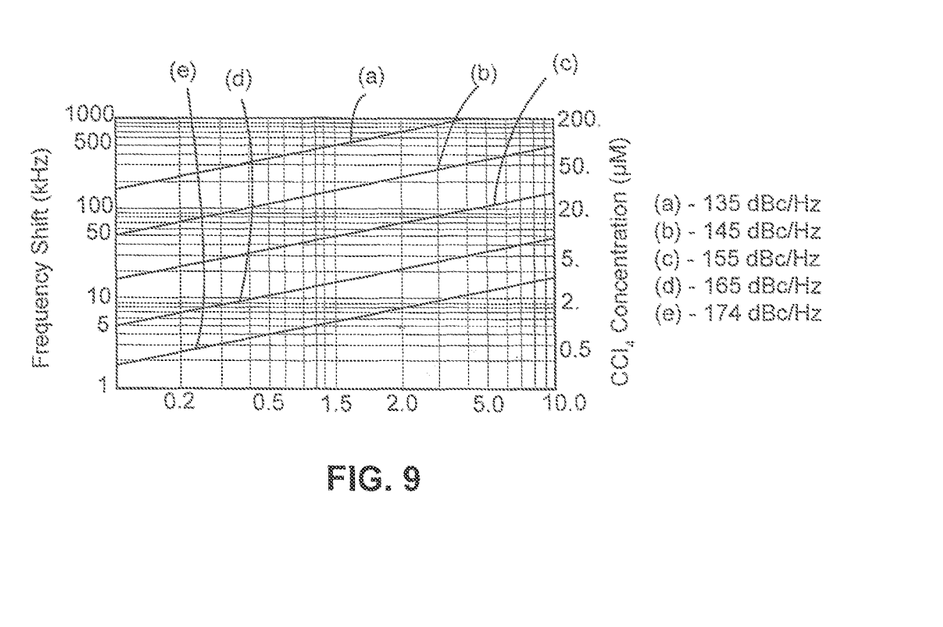
FIG. 9 shows graphs of the minimum frequency shift as a function of measurement bandwidth for several oscillator phase noise levels, from −135 dBc/Hz (Curve a) to the thermal noise floor (−174 dBc/Hz, for a signal power of 0 dBm) in Curve e.

To find the sensitivity of the detection system in the presence of the above-described noise (for the apparatus shown in the FIG. 3 specific implementation, but not representative of fundamental limits), the change in delay as a function of change in center frequency, $\delta\tau = \varphi_2 \delta\omega$, will be used. This delay change corresponds to a phase change of $\phi(\tau) = 2\pi f_r \varphi_2 \delta\omega$. Equating this phase change to the phase noise for various levels, we can solve for the minimum frequency shift as $$\delta\omega = \frac{\sqrt{2 \times 10^{\frac{L(f)}{10}} \Delta f}}{2\pi m f_r \varphi_2},$$

where a bandwidth narrow enough that the power spectrum does not change appreciably over the bandwidth has been assumed. The minimum detectable frequency is calculated for 20.5 km of fiber and our 36.7 MHz fundamental (m=1) repetition rate as a function of measurement bandwidth and oscillator phase noise in FIG. 9. The dispersion of SMF-28e is D=18 ps/nm/km ($\beta_2$=−23 ps$^2$/km), so $\varphi_2$ for 20.5 km of fiber is ~471 ps$^2$. The oscillator runs at 24$^{th}$ the harmonic of the repetition rate, 880 MHz, with an output power of 6 dBm. The phase noise is from the oscillator is −145 dBc/Hz for a 100 kHz offset. Dividing this down to the repetition rate introduces a small amount of additive phase noise, $S_D$.

Having generally described the invention, the following EXAMPLE provides greater detail.

EXAMPLE

Figure 10A:
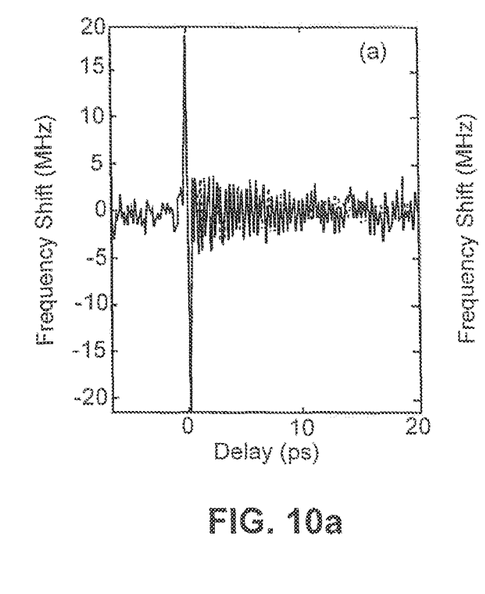
Figure 10B:
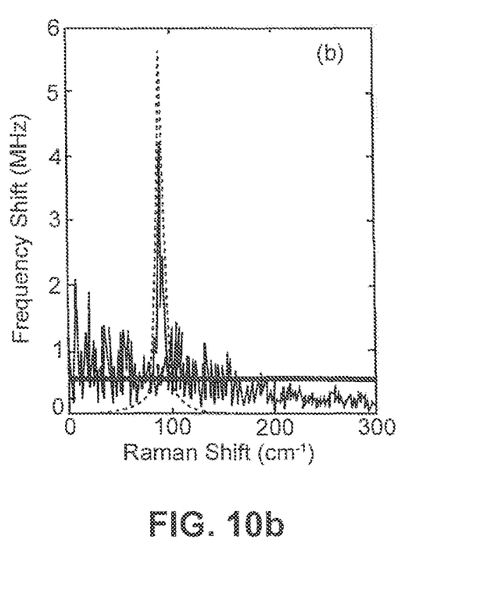
FIG. 10b is a graph of the Lorentzian Raman line from the predicted parameters plotted (dotted curve) along with the Fourier transform of the temporal data (solid curve), and the residual noise left by subtracting the predicted trace from the data and Fourier transforming (dashed curve), the theoretical Optical PLL noise floor being calculated using the measured RF noise floor, shown in FIG. 7, and shown as a solid line (thick solid curve).

Raman Measurements:

The example Raman experiment uses a pump pulse to excite a transient change in the index of refraction which is sampled by a probe pulse. The time delay between the pump pulse and the probe pulse can be varied to observe the time dependence of the material response using the probe pulse. The pump pulse can be modulated in amplitude, which will modulate the detected probe signal. The phase signal is measured using a lock-in amplifier, locked to the pump amplitude modulation frequency, while varying the pump-probe delay. The measured voltage $V_{meas}$ is proportional to the phase difference between the Optical PLL signal and the reference oscillator though the conversion slope of the double balanced mixer, $K_{d,mix}$, as $V_{meas}$=$K_{d,mix}$ $\Delta\phi$. Rearranging, the frequency shift can be written as:

$$\delta\omega = \frac{V_{meas}}{2\pi\, m\, f_r\, \varphi_2\, K_{d,mix}},$$

where $\Delta\phi$ is the phase difference. The phase signal can then be related to the frequency shift through the repetition rate ($f_r$) and the GDD ($\varphi_2$). However, an exact value for the Group Delay Dispersion, GDD, is unknown for the apparatus, as the length and exact dispersion of the fiber are both unknown. While the GDD of a short length of fiber and the length of the fiber may be measured, these measurements are quite cumbersome and their accuracy might still be suspect. To avoid this, the apparatus is calibrated by relating the signal measured using the Optical PLL to a measurement made of a Raman sample producing large signals using a conventional measurement approach. This method provides a reliable cross calibration between the two techniques. A pump-probe delay scan of the BGO crystal is taken at a pump power of 3 mW, yielding the data shown in FIG. 10. The measured data shows good agreement with the predicted noise floor for this data, though the noise floor is not flat, indicating a deviation from the white noise expected in the shot noise limit.

FIG. 10 is the example data showing this measurement technique in use for the measurement of Raman data by transforming the frequency shifts into time shifts. This was done quite sensitively. A well-defined Raman peak at 90 wavenumbers may be observed, where it is expected to be. The height of this line is proportional to the strength of the excitation pulse, which is quite weak in this case, simulating a weak interaction from a dilute sample. These data show this measurement having been made in an entirely new way, which is already at or slightly better than the state of the art techniques, and having significant scalability as described. That is, the sensitivity represents only a few fold increase over existing approaches. However, while those approaches have reached their fundamental noise-limited sensitivity, the current operation of this method has not been optimized. The phase noise floor is almost 20 dB above the shot-noise limited floor, with the noise floor currently being limited by other components. By choosing other components having lower noise at the frequencies of interest, and/or increasing the optical and/or RF power, operation nearer the shot-noise limit, is expected, thereby increasing the sensitivity over the demonstrated value.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

REFERENCES

[1] E. N. Ivanov, S. A. Diddams, and L. Hollberg, "Analysis of Noise Mechanisms Limiting the Frequency Stability of Microwave Signals Generated With a Femtosecond Laser," *IEEE J. Sel. Top. Quantum Electron.*, vol. 9, no. 4, pp. 1059-1065, 2003.

[2] F. Quinlan, T. M. Fortier, H. Jiang, A. Hati, C. Nelson, Y. Fu, J. C. Campbell, and S. A. Diddams, "Exploiting shot noise correlations in the photodetection of ultrashort optical pulse trains," *Nat. Photonics*, vol. 17, pp. 290-293, 2013.

[3] J. Kim, F. X. Kärtner, and M. H. Perrott, "Femtosecond synchronization of radio frequency signals with optical pulse trains," *Opt. Lett.*, vol. 29, no. 17, pp. 2076-8, September 2004.

[4] W. Kim and A. Majumdar, "Phonon scattering cross section of polydispersed spherical nanoparticles," *J. Appl. Phys.*, vol. 99, no. 8, p. 084306, 2006.

[5] K. Jung and J. Kim, "Subfemtosecond synchronization of microwave oscillators with mode-locked Er-fiber lasers.," *Opt. Lett.*, vol. 37, no. 14, pp. 2958-60, July 2012.

[6] W. H. Steier, "A Push-Pull Optical Amplitude Modulator," *IEEE J. Quantum Electron.*, vol. QE-3, no. 12, pp. 664-667, 1967.

[7] S. Dubovitsky, W. H. Steier, S. Yegnanarayanan, and B. Jalali, "Analysis and Improvement of Mach-Zehnder Modulator Linearity Performance for Chirped and Tunable Optical Carriers," *J. Light. Technol.*, vol. 8724, no. May, pp. 886-891, 2002.

[8] T. M. Fortier, C. W. Nelson, a. Hati, F. Quinlan, J. Taylor, H. Jiang, C. W. Chou, T. Rosenband, N. Lemke, a. Ludlow, D. Howe, C. W. Oates, and S. a. Diddams, "Sub-femtosecond absolute timing jitter with a 10 GHz hybrid photonic-microwave oscillator," *Appl. Phys. Lett.*, vol. 100, no. 23, p. 231111, 2012.

[9] J. Kim and F. X. Kärtner, "Attosecond-precision ultrafast photonics," *Laser Photon. Rev.*, vol. 4, no. 3, pp. 432-456, April 2010.

What is claimed is:

1. A method for measuring a shift in a center optical frequency of light from a light source, from that of a known center optical frequency, the method comprising:
   directing the light, having a shifted center optical frequency, into an optically dispersive system, whereby the light having the shifted center optical frequency experiences a first transit time through the dispersive system;
   measuring the first transit time;
   directing control light having the known center optical frequency into the optically dispersive system, whereby the control light having the known center optical frequency experiences a second transit time through the dispersive system;
   measuring the second transit time;
   generating a time delay from a difference of the first transit time and the second transit time; and
   determining the shift in the center optical frequency based on the time delay.

2. The method of claim 1, wherein the optically dispersive system is chosen from optical fibers, bulk materials, volumetric or fiber Bragg gratings, and grating or prism based pulse stretchers.

3. The method of claim 1, wherein the light source generates optical pulses, each pulse having a center optical frequency.

4. The method of claim 3, wherein said step of measuring the first transit time comprises converting the optical pulses into periodic electronic pulsed signals, and measuring the phase of the periodic electronic pulsed signals relative to a reference electronic oscillator clock, whereby the time delays of the pulses are determined.

5. The method of claim 3, wherein said step of measuring the second transit time and comprises converting the optical pulses into periodic electronic pulsed signals, and measuring the phase of the periodic pulsed signals relative to a reference electronic oscillator clock, whereby the time delays of the pulses are determined.

6. The method of claim 4 or 5, wherein the time delay is measured using a method chosen from Optical Phase-Locked Loop, intensity cross correlation, and direct pulse train measurement.

7. The method of claim 4 or 5, wherein said step of converting the optical pulses into periodic electronic pulsed signals is achieved by directing the optical pulses onto a photodetector.

8. The method of claim 4 or 5, wherein said step of measuring the phase of the periodic pulsed signals is achieved using electronic oscillator phase detection.

9. An apparatus for measuring a shift in a center optical frequency of light from a light source, from that of a known center optical frequency, the apparatus comprising:
   an optically dispersive system for receiving light from said light source, whereby light having a shifted center optical frequency travels through said dispersive system in a first time period, different from a second time period for control light having the known center optical frequency to travel through said dispersive system; and
   means for measuring the first time period;
   whereby a difference between the first time period and the second time period is determined and is indicative of the shift of the center optical frequency relative to the known center optical frequency.

10. The apparatus of claim 9, wherein said optically dispersive system is chosen from optical fibers, bulk materials, volumetric or fiber Bragg gratings, and grating or prism based pulse stretchers.

11. The apparatus of claim 9, wherein said light source generates optical pulses, each pulse having a center optical frequency.

12. The apparatus of claim 11, further comprising at least one photodetector wherein the optical pulses are converted into periodic electronic pulses.

13. The apparatus of claim 12, wherein said means for measuring the first time period comprises means for measuring the phase of the periodic electronic pulses.

14. The apparatus of claim 13, wherein said phase measurement means comprises apparatus for electronic oscillator phase detection.

15. The apparatus of claim 11, wherein said means for measuring the first time period comprises an Optical Phase-Locked Loop apparatus.

16. The apparatus of claim 11, wherein said means for measuring the first time period comprises apparatus for direct pulse train measurement.

17. A method comprising:
   directing first light having a first center optical frequency into an optically dispersive system, whereby the first light having the first center optical frequency experiences a first transit time through the dispersive system;
   measuring the first transit time;
   determining a time delay between the first transit time and a second transit time corresponding to second light having a second center optical frequency; and
   based on the time delay, determining a difference between the first center optical frequency and the second center optical frequency.

18. The method of claim 17, further comprising the steps of:
   directing the second light having the second center optical frequency into the optically dispersive system, whereby the second light having the second center frequency experiences the second transit time through the dispersive system; and
   measuring the second transit time.

19. The method of claim 17, wherein the optically dispersive system is chosen from optical fibers, bulk materials, volumetric or fiber Bragg gratings, and grating or prism based pulse stretchers.

20. The method of claim 17, wherein the first light is generated by a light source and wherein the light source generates optical pulses, each pulse having a center optical frequency.

21. The method of claim 20, wherein said step of measuring the first transit time comprises converting the optical pulses into periodic electronic pulsed signals, and measuring the phase of the periodic electronic pulsed signals relative to a reference electronic oscillator clock, whereby the time delays of the pulses are determined.

22. The method of claim 18, wherein the first light is generated by a light source and wherein the light source generates optical pulses, each pulse having a center optical frequency and said step of measuring the second transit time comprises converting the optical pulses into periodic electronic pulsed signals, and measuring the phase of the periodic pulsed signals relative to a reference electronic oscillator clock, whereby the time delays of the pulses are determined.

23. The method of claims 21 or 22, wherein the time delay is measured using a method chosen from Optical Phase-Locked Loop, intensity cross correlation, and direct pulse train measurement.

24. The method of claim 21 or 22, wherein said step of converting the optical pulses into periodic electronic pulsed signals is achieved by directing the optical pulses onto a photodetector.

25. The method of claim 21 or 22, wherein said step of measuring the phase of the periodic pulsed signals is achieved using electronic oscillator phase detection.

* * * * *